United States Patent [19]

Beaver et al.

[11] Patent Number: 4,748,121

[45] Date of Patent: May 31, 1988

[54] POROUS GLASS FIBERS WITH IMMOBILIZED BIOCHEMICALLY ACTIVE MATERIAL

[75] Inventors: Richard P. Beaver, Library; Ronald E. Betts, Turtle Creek; Lin-Chang Chiang, Export; George V. Sanzero, New Kensington, all of Pa.

[73] Assignee: PPG Industries, Inc., Pittsburgh, Pa.

[21] Appl. No.: 677,108

[22] Filed: Nov. 30, 1984

[51] Int. Cl.$^4$ .................. C12N 11/00; C12N 11/14; G01N 33/552; C07K 17/14

[52] U.S. Cl. ................................ 435/176; 435/174; 436/527; 530/811

[58] Field of Search .............. 65/3.1, 10.1; 435/174, 435/176, 177, 181, 241; 436/527; 530/811

[56] References Cited

U.S. PATENT DOCUMENTS

| | | | |
|---|---|---|---|
| 2,106,744 | 2/1938 | Hood et al. | 106/36.1 |
| 2,215,039 | 9/1940 | Hood et al. | 49/79 |
| 2,221,709 | 11/1940 | Hood et al. | 106/36.1 |
| 2,286,275 | 6/1942 | Hood et al. | 49/79 |
| 2,401,841 | 2/1949 | Nordberg | 49/79 |
| 2,480,672 | 8/1949 | Plank | 49/79 |
| 2,491,761 | 12/1949 | Parker et al. | 41/42 |
| 2,494,259 | 1/1950 | Nordberg | 106/50 |
| 2,500,092 | 3/1950 | Parker et al. | 41/42 |
| 2,635,390 | 4/1953 | Parker | 49/79 |
| 2,843,461 | 7/1958 | Labino | 41/42 |
| 3,231,540 | 1/1966 | Vanderbilt | 260/41.5 |
| 3,519,538 | 7/1970 | Messing et al. | 195/63 |
| 3,549,524 | 12/1970 | Haller | 210/31 |
| 3,556,945 | 1/1971 | Messing | 195/63 |
| 3,650,721 | 3/1972 | Hammel et al. | 65/31 |
| 3,652,761 | 3/1972 | Weetall | 424/12 |
| 3,666,627 | 5/1972 | Messing | 195/68 |
| 3,669,841 | 6/1972 | Miller | 195/63 |
| 3,687,850 | 8/1972 | Gagin | 252/62 |
| 3,783,101 | 1/1974 | Tomb et al. | 195/63 |
| 3,802,997 | 4/1974 | Messing | 195/68 |
| 3,804,719 | 4/1974 | Messing | 195/68 |
| 3,809,605 | 5/1974 | Schmitt et al. | 162/158 |
| 3,841,969 | 10/1974 | Emery et al. | 195/63 |
| 3,841,971 | 10/1974 | Messing | 435/176 |
| 3,843,341 | 10/1974 | Hammel et al. | 65/22 |
| 3,850,751 | 11/1974 | Messing | 435/176 |
| 3,892,580 | 7/1975 | Messing | 106/41 |

(List continued on next page.)

FOREIGN PATENT DOCUMENTS

| | | |
|---|---|---|
| 2309440 | 3/1972 | Fed. Rep. of Germany ........ 501/65 |
| 3033076A1 | 4/1982 | Fed. Rep. of Germany . |
| 141035 | 10/1982 | Fed. Rep. of Germany . |
| 22650 | 3/1981 | Japan . |
| 56-22654 | 3/1981 | Japan ..................... 501/65 |
| 58-74538 | 5/1983 | Japan ..................... 501/77 |
| 1066257 | 4/1967 | United Kingdom . |
| 1491261 | 11/1977 | United Kingdom . |
| 1557074 | 12/1979 | United Kingdom . |

OTHER PUBLICATIONS

Koho, K. T., Chemical Abstracts, vol. 100:171175y, 5/21/84, p. 324.

(List continued on next page.)

Primary Examiner—David M. Naff
Attorney, Agent, or Firm—Kenneth J. Stachel

[57] ABSTRACT

Biochemically active material is immobilized on porous silica-rich glass fibers having a diameter of about 3 to 150 microns, a length of about 0.03 inch to continuous fiber length, a mean pore diameter in the range of about 10 to 3000 angstroms, a pore volume of about 0.5 to 1.5 cc/gm and a surface area of about 10 to 600 m$^2$/gm. The porous glass fibers are preferably formed from a composition containing greater than 35 up to 60 weight percent B$_2$O$_3$, about 1 to 10 weight percent alkali metal oxides, about 30 to 65 weight percent SiO$_2$, up to about 5 weight percent ZrO$_2$, and up to about 4 weight percent Al$_2$O$_3$. Fibers having the composition are heated to cause phase separation into a boron-rich phase and a silica-rich phase, and are then treated by water and acid leaching to produce the porous glass fibers. A biochemically active material is attached to the fibers by absorption or by covalent bonding with a linking agent.

9 Claims, 2 Drawing Sheets

U.S. PATENT DOCUMENTS

| | | | |
|---|---|---|---|
| 3,910,823 | 10/1975 | Messing | 195/63 |
| 3,923,533 | 12/1975 | Hammel et al. | 106/54 |
| 3,923,688 | 12/1975 | Hammel et al. | 252/432 |
| 3,930,950 | 1/1976 | Royer | 195/63 |
| 3,930,951 | 1/1976 | Messing | 195/63 |
| 3,933,589 | 1/1976 | Keyes | 195/68 |
| 3,945,816 | 3/1976 | Johnson | 65/22 |
| 3,972,720 | 8/1976 | Hammel et al. | 106/54 |
| 3,972,721 | 8/1976 | Hammel et al. | 106/40 V |
| 3,983,000 | 9/1976 | Messing et al. | 195/63 |
| 4,002,445 | 1/1977 | Graham | 65/3.1 |
| 4,006,059 | 2/1977 | Butler | 195/68 |
| 4,008,126 | 2/1977 | Keyes | 195/63 |
| 4,024,235 | 5/1977 | Weetall et al. | 424/1 |
| 4,025,667 | 5/1977 | Tomb et al. | 427/215 |
| 4,042,359 | 8/1977 | Schnabel et al. | 65/2 |
| 4,049,411 | 9/1977 | Long et al. | 65/10.1 |
| 4,071,339 | 1/1978 | Griffiths | 65/3.1 |
| 4,086,074 | 4/1978 | Minot et al. | 65/31 |
| 4,112,032 | 9/1978 | Elaszyk et al. | 264/42 |
| 4,169,761 | 10/1979 | Preczustz et al. | 435/235 |
| 4,177,038 | 12/1979 | Biebricher et al. | 8/192 |
| 4,187,094 | 2/1980 | Lu et al. | 65/30 |
| 4,323,650 | 4/1982 | Rosevear | 435/174 |
| 4,352,884 | 10/1982 | Nakashima et al. | 435/180 |
| 4,357,142 | 11/1982 | Schall, Jr. et al. | 23/230 B |
| 4,363,634 | 12/1982 | Schall, Jr. | 23/230 B |
| 4,371,612 | 2/1983 | Matsumoto et al. | 435/44 |
| 4,397,913 | 8/1983 | Fahey | 65/3.1 X |
| 4,415,663 | 11/1983 | Symon et al. | 435/176 |
| 4,415,664 | 11/1983 | Barszcz et al. | 435/176 |
| 4,425,434 | 1/1984 | Rosevear | 435/176 |
| 4,519,538 | 7/1985 | Messing et al. | 195/63 |

OTHER PUBLICATIONS

Glassy, et al., J. Immunol. Methods, 58 (1–2), 1983, pp. 119–126.

"Decomposition of Urea by Size-Fractionated Planktonic Community in a Eutrophic Reservoir in Japan", by Satoh, Hydra Bil-ogia, vol. 83, 1981.

"Relationship of Pore Size and Surface Area to Quantity of Stabilized Enzyme Bound to Glass", by Ralph A. Messing, Enzymologia, vol. 39, 1970.

"Trypsin and Papain Covalently Coupled to Porous Glass: Preparation and Characterization", Abstract, Science, vol. 166, 1969.

"A Gas-Liquid Solid Phase Peptide and Protein Sequenator", Rodney M. Hewick et al., The Journal of Biological Chemistry, vol. 256, pp. 7990–7997.

Fibre-Entrapped Enzymes, Process Biochemistry, Aug., 1972, D. Dinelli, pp. 9–12.

Immobilized Enzymes in Analytical and Clinical Chemistry, Peter W. Carr and Larry D. Bowers, John Wiley & Sons Publishers, vol. 56, pp. 168–169.

POROUS GLASS FIBERS WITH IMMOBILIZED BIOCHEMICALLY ACTIVE MATERIAL

The present invention is directed to controlled porous glass fibers with biochemically active material immobilized both on the external and/or internal surfaces of the glass fibers and the method of producing same.

With increasing interest, various chemical, biochemical and/or biological processes are being investigated, developed or used, where biochemically active materials sare employed in various roles in the processes. Generally, the role is in modifying a starting material to produce a product such as through action as an initiator, catalyst or the like. One such example of a biochemically active material is enzymes which are biochemical macromolecules with extraordinary properties of specificity in catalytic power to catalyze various chemical reactions.

The feasibility of large scale commercial use of such biochemically active material is hampered by economics and limited stability of some material to mechanical and chemical changes in their environment. To circumvent these difficulties, the art has suggested immobilizing the biochemically active material on sundry supports. Such immobilization offers stability, reusability and recyclability of the biochemically active material. The supports mentioned in the art for immobilization include polymeric material such as fibers and also inorganic surfaces such as beads and fibers. The various support material all have their particular advantages and disadvantages for immobilization. The art has suggested that glass supports have not always found universal use because of their limited capacity to bond or absorb biochemically active material, whereas polymeric materials have a higher affinity for bonding or absorbing biochemically active material. Several disadvantages of the numerous organic supports are their sensitivity to microbial attack, their lower thermal stability that reduces the possibility of sterilizing the polymeric supports, and their poor dimensional stability as elevated temperatures such that the support may be deformed, distorted or destroyed at such elevated temperatures.

In U.S. Pat. No. 3,519,538 (Messing et al.) and 4,024,235 (Weetall et al.), methods are disclosed for bonding biomaterial directly to glass or ceramic supports such as beads by incorporating derivatives of silane compounds into the siliceous surfaces of the glass or ceramic and chemically coupling biologically or biochemically active molecules through the organic moiety of the organo silane. U.S. Pat. No. 3,642,761 (Weetall) discloses a method, whereby organic biological or immunological material can be bonded to inorganic supports such as glass beads through the use of the organo silane material. Also U.S. Pat. No. 3,669,841 (Miller) discloses the use of a crosslinking agent to covalently attach enzymes to silylated siliceous material. These siliceous materials include fibrous silica and silicates such as glass cloth, fibers, and matting. In this method, a silane coupling agent in an inert solvent or aqueous solution is applied to the inorganic surface and crosslinked with a crosslinking agent such as glutaraldehyde.

In the book entitled "Immobilized Enzymes and Analytical and Clinical Chemistry", by Pierre W. Car, Ph.D. and Larry D. Bowers, Ph.D., Volume 56, pages 168 and 169 it is reported that the controlled-porosity inorganic bead supports from Corning Glass Works are by far the best support material for enzyme immobilization. Their narrow pore-size distribution and optimum pore size and surface area have overcome the previously identified disadvantage of inorganic supports to have only a limited capacity to bond or absorb biomaterial. It has also been reported that the inorganic supports continue to have the disadvantages of too strong an interaction between some proteins and silica causing denaturation of some enzymes, and of an initial cost factor that without regeneration is 4 to 5 times as expensive as the organic polymeric supports for immobilization of biochemically active material.

It is an object of the present invention to provide porous glass fiber supports having immobilized biochemically active material, where the support has a large surface area and can be prepared to have a high mechanical strength and good characteristics for use in process reactors.

SUMMARY OF THE INVENTION

The present invention accomplishes the aforementioned object and other objects gleaned from the following disclosure by producing porous glass fibers of any length which have immobilized biochemically active material. The method for producing these glass fibers involves forming glass fibers from a fiberizable glass forming batch composition formulated to result in pore generating glass compositions, attenuating the fibers, generating pores in the fibers and immobilizing the biochemically active material on and/or in the fibers.

The porous glass fibers with immobilized biochemically active materials are either hollow or solid silica-rich fibers. The fiber diameter can range from less than around 3 microns to around 150 microns or more. The lengths can vary from mere particles to discrete lengths of less than an inch, including as low as around 0.03 inch (0.08 cm) to any continuous fiber lengths. All of the fiberous material maintain at least a semblance of fiber characteristics ranging from a fiberous curvature for particles from fractured or broken fiber lengths to a complete fiber cylindrical form for the discrete lengths of fibers. The mean pore diameter of the majority of pores in the fibers can range from about 10 angstroms to about 3,000 angstroms. The biochemically active material immobilized on and/or in the fibers are maintained in an active state by the fibers being surrounded with a stabilizing fluid and/or temperature environment.

DETAILED DESCRIPTION OF THE INVENTION

Figure 1:
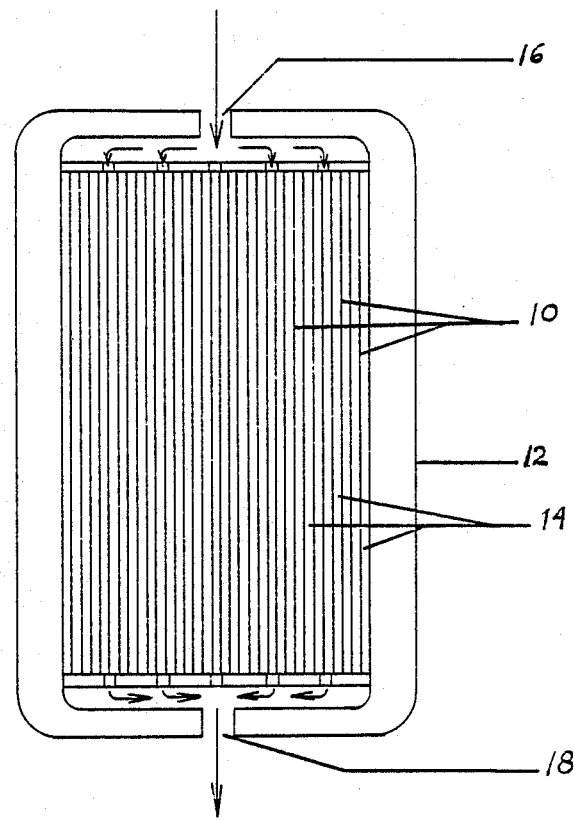
FIG. 1 is a lengthwise, traverse, sectional view of a reactor packed with glass fibers with immobilized biochemically active material prepared in accordance with the present invention.

For better understanding in the following disclosure and in the claims of the present application, the following terms have the following definitions.

The term "biochemically active material" refers to natural or synthetic substances which are either biological or biochemical substances, or materials which are capable of interacting with a biological or biochemical substance, or material produced from a biochemical or biological substance, where these materials have chemical, biochemical or biological activity, catalytic activity or production capability. Nonexclusive examples of the biochemically active material include proteins; nucleic acids; nucleoproteins; polynucleotides; polynucleosides; lipoproteins; isozymes; lysozymes; co-enzymes including co-factors and prosthetic groups; hormones; endorphins; enkaphlins; peptides; apoenzymes; organic or inorganic matter constituting substrates for enzymes; hybridomas, antibodies including monoclonal antibodies; antigens; immunoglobulins; antigen-antibody complexes; lymphokines; and other immunological material; viruses; plasmids; growth factors; antibiotics; and living, dead and genetically transformed prokaryotic and eukaryotic cells such as bacterial, yeast, mold, fungi, plant, and animal cells including mammalian cells; bound dependent cells such as cells from insects, fish, reptiles, aves, mammals and other vertebrates and invertebrates where such cells, for instance, can be brain cells, epithelial cells, lung cells, heart cells, fibroblast cells, embryonic cells and cells from other organs of these creatures; and parts of cells such as cytoplasm, ectoplasm, endoplasm, karyolymp, karylosomes, nucleoli, chromatin, chondriosomes, mitrochondria, golgi bodies or trophospongium, where the parts of the cells or dead cells are capable of conducting or participating in at least one of the following chemical reations, biological interactions, metabolism, growth, response to stimuli and reproduction. Typical examples of biochemically active proteins are various enzymes, nonexclusive examples of which include: oxidoreductases, hydroxylases, hydrolases, transferases, lyases, isomerases, ligases, etc. Examples of transferases are cretin phosphokinase, glycerol kinase, pyruvate kinase, hexokinase, etc. Examples of isomerases are glucose phosphate isomerase, alanine isomerase, glucose isomerase, etc. Typical examples of ligase is glutathione synthetase. Example of hydrolase are creatininase, cretinase, cephalosporinase, penicillinase, cephalosporin acylase, penicillin acylase, aminoacylase, urease, bromelein, papaine, chymotrypsin, trypsin, pepsin, galactosidase, glucosidase, amylase, phosphatase, cholesterolesterase, acetylchlolineesterase, phospholipase, lipase, etc. Examples of oxidoreductases are lipoxygenase, catalase, peroxidase, uricase, diaphorase, sarcosine oxidase, amine oxidase, amino acid oxidase, glutamic acid dehydrogenase, pyruvic acid oxidase, chlolineoxidase, galactoseoxidase, cholesteroloxidase, glucoseoxidase, 3-hydroxybutyrate dehydrogenase, glucose-6-phosphase dehydrogenase, galactose dehydrogenase, lactate dehydrogenase, glycerol phosphate dehydrogenase, glycerol dehydrogenase, alcohol dehydrogenase, biochemically or chemically modified enzymes and synthetic enzymes and the like.

The meaning of the term "related materials" for biochemically active material refers to nutrients, culture medium, stabilizing fluid either liquid or gaseous, for living biochemically active material and products of biochemically active material.

The meaning of the term "minimum exclusion diameter", hereinafter called MED, refers to the smallest or narrowest cross-section in a three dimensional form of the material such as the biochemically active material and linking agents and related material and including symmetrical and asymmetrical shapes and those shapes which these materials may have under normal deformation. The MEDs can be determined by any method known to those skilled in the art. For instance, the molecular weight of the biochemically active material or related material is determined or approximated and the mean pore diameter is calculated to be at least equal to or greater than the square root of the molecular weight, where the surface area of the fiber is greater than at least 0.1 $m^2/gm$.

"Substantial portion of water and/or acid leachable material", means around 80 percent or more of the water and/or acid leachable material. Such materials are exemplified by boron-containing materials such as boron, boron oxides and/or anhydrides and alkali metal borates.

"Internal surface area", means the surface area of the pores of the glass fibers and any hollow lumen of hollow glass fibers.

The porous glass fibers or filaments, hereinafter referred to as fibers, of the present invention with the immobilized biochemically active material are prepared from a formulated fiberizable, pore generating glass forming batch composition. The batch composition is formulated to enable the resulting glass fibers to have two groups of components. Typical batch material known to those skilled in the art can be used and calculated by known methods to produce the glass compositions with components of two groups. Here the term "group" is used in the figurative sense for reference. In the pore generating glass fiber composition, the group of water and/or acid leachable components includes one or more boron-containing materials, alkali metal oxides, alkaline earth metal oxides and some metal oxides like aluminum oxide. Non-water and hydrofluoric acid, and essentially non-acid, except for phosphoric acid, leachable components include the siliceous material such as silica and glass modifiers like aluminum, zirconium, titanium and the like. The glass fibers may be heat treated to engender phase separation of the glass into a phase of water and/or acid leachable components and a phase of siliceous material with any appropriate glass modifier. Such phase separation should occur prior to leaching and such phase separation will depend on the composition and structure of the glass fibers. Of the water and/or acid leachable components, the concentration of boron-containing material in the glass can range from 0 to about 60 weight percent. The amount of boron-containing material should not be too great that the softening point of the glass fibers is decreased to cause the fibers to stick together during heat treatment. This tackiness complicates the maintenance of individual fiber identity and, for discrete lengthy fibers, maintenance of at least near parallel alignment during subsequent processing steps. Usually, the heat treatable glass compositions requiring phase separation before leaching are those having high concentrations of boron-containing materials, i.e. 20 to around 60, preferably 35 to around 60, weight percent of the total glass composition. The amount of the water and/or acid leachable group in the glass fiber composition should be at least around 15 volume percent, and preferably at least around 20 volume percent of the total glass composition.

When the content of boron-containing material is 0 or around zero, the amount of alkali metal oxide (RO) is the major component of the water and/or acid-leachable components. When the amount of boron-containing compound is in the range of about 4 to about 35 weight percent of the total resulting glass composition, one or more water and/or acid leachable inorganic oxides and/or one or more RO compounds can be present in the group. When the amount of boron-containing material is around 30 or 35 weight percent and up to 60 weight percent and especially around 40 to around 60 weight percent of the total resulting glass composition, the boron-containing material and RO compounds constitute the majority of the aforementioned group.

The amount of siliceous material should not be less than around 25 and preferably not less than 30 weight percent of the total glass composition. Generally, the siliceous material is less than around 85, preferably less than around 70 weight percent of the total glass composition. The amounts of any other components known to those skilled in the art to be nonleachable by water and/or acids can be in the non-water and non-acid leachable group in art recognized amounts. In addition, trace amounts of generally less than 1 weight percent of art recognized impurities may also be present in the glass composition. The formulation of the glass forming batch results in glass fibers wherein pores can be generated, whether by heat treating and water and/or acid leaching, or acid leaching alone, or either of these nonalkaline leaching approaches followed by alkali leaching to yield a pore volume in the range of about 0.5 to about 1.5 and preferably about 0.8 to about 1.2 cc/gm, and most preferably about 0.8 to about 1 cc/gm.

The glass batch formulation is constituted to meet the requirements of mean pore diameter and pore volume in the glass fibers. The requisite mean pore diameter is dependent on the MED of the related material for the living biochemically active material, or the nonliving biochemically active material alone, or of the biochemically active material in addition to any chemical attaching agents. With the determination of the proper mean pore size to accommodate the related material or biochemically active material and any attaching agent to be immobilized, the number of pores resulting from formulating the batch gives good loadings of the related material or biochemically active material. The number of pores is expressed as pore volume and surface area, and for discrete lengthy fibers, the volume should not be too large to destroy the fiberous shape over a discrete length. Such a length can range from that of chopped fibers up to any length that can be collected in the production of continuous glass fibers. As the discrete length of the glass fibers gets longer than chopped fibers, the pore volume should not extend beyond about 1.2 cc/gm and preferably 1.0 cc/gm. This maintains the discrete length of glass fiber and does not engender breakage of the discrete lengths to smaller lengths. Of course, higher pore volumes can be used to result in fiber particulates. It is preferred in the present invention that the glass batch composition is formulated to yield the requisite mean pore diameter and volume from the water and/or acid leachable components in the glass formulation. In this manner, the silica need not be leached to attain the desired mean pore diameter and pore volume, and the silica can provide the requisite mechanical strength to achieve longer length fibers.

A particularly useful glass composition is a heat treatable glass for phase separation having a low silica and high-borate content. Such a glass has the following constituents: silica at 30 to 50 percent by weight, boric oxide at 40 to 55 percent by weight, alkali metal oxide at 5 to 15 percent by weight, and aluminum oxide from 0 to 4 weight percent. Further nonexclusive examples of phase separable, borosilicate glasses are described in U.S. Pat. Nos. 2,106,744; 2,215,039 and 2,221,709 and 2,286,275, 3,972,720; 3,843,341 and 3,923,688, all of which are hereby incorporated by reference. The most preferred glass composition contains boric oxide at 54 weight percent, sodium oxide at 8.0 weight percent and silica at 38 weight percent.

Glass compositions which may not require heat treatment for phase separation of the glass are also useful. Such fiberizable glass compositions have leachable material which can be boron-containing material and/or alkali metal oxides and alkaline earth metal oxides that are leachable by acid leaching and alkali leaching. Examples of these types of glass compositions are described in U.S. Pat. Nos. 2,334,961 and 2,571,074, hereby incorporated by reference.

The glass batch compositions are melted in a furnace at temperatures and times to obtain a fiberizable viscosity for the molten glass. Generally, the batch is heated to 2000°F. (1093° C.) to 3000° F. (1649° C.) for 1 hour to about 6 hours or longer. The molten glass is attenuated from the orifices of a bushing or spinnerets located on a forehearth connected to the furnace. The attenuation is conducted by mechanical means (winding or chopping) or thermal means by using heated fluid flow. Where the fibers are formed and attenuated as hollow glass fibers, they can be formed and attenuated by methods described in U.S. Pat. Nos. 3,268,313; 3,421,873; 3,510,393, all of which are hereby incorporated by reference. Any other method of forming and attenuating the fibers as known by those skilled in the art can also be used. The fibers may be cooled, treated with a chemical protecting agent, i.e., a sizing composition, and gathered into one or more strands and chopped or collected as continous fibers or strands by any method known to those skilled in the art. U.S. Pat. Nos. 4,071,339 and 4,049,411, incorporated herein by reference are typical of such methods.

The glass fibers can have, and usually do have, a sizing composition applied to the glass fibers which protects the glass fibers from interfilament abrasion in further processing steps. The sizing composition can be applied in art known quantities by any method known to those skilled in the art. The sizing composition is usually an aqueous composition with water soluble, dispersible or emulsifiable chemical agents that is placed on the glass fibers and remains on the glass fibers after the water and/or solvent is evaporated, but that may also be easily removable through solubility in water. An example of a suitable water soluble chemical treatment is a cationic lubricant in water which is applied to the glass fibers. A suitable cationic lubricant includes Cation X ® material, which is an alkyl imidazoline reaction product of tetraethylene pentamine and stearic acid. Other suitable material include textile softeners and cationic lubricants or agents generally known to those skilled in the art such as those disclosed in U.S. Pat. No. 4,002,445 (Graham) hereby incorporated by reference.

After the sizing composition is applied to the glass fibers, the fibers are gathered into one or more strand, usually by means of a gathering shoe and then the glass fibers are wound onto a rotating drum-type winder having a forming tube to produce a forming package. The collet on which the forming package rides usually rotates at high speeds to collect the strand or strands into the forming package. Such speeds can be upward of 4,400 revolutions per minute which continues until the winder is slowed to a stop and the forming package is removed. An example of the forming process including sizing, gathering and collecting the glass fibers into a forming package is disclosed in U.S. Pat. No. 4,071,339 (Griffiths) and U.S. Pat. No. 4,049,411 (Long and Dent) where attenuation speeds of from about 2,000 to 20,000 feet per second are achieved, both patents are hereby incorporated by reference.

The glass fibers and/or strands that are collected into the forms of multilayered package, either forming packages or roving packages, or into the forms of chopped fibers or strands, chopped or continuous fiberous or strand mats or batts are treated for pore generation. The fibers or strands may be removed from the packages by cutting or rewinding onto larger diameter drums or can remain in the packages, mat, batt or chopped strand form for the generation of pores. Preferably the strands are cut from one or more multilayered packages by making one or more cuts through the layers in a lengthwise manner extending parallel to the lengthwise axis of the package. The length of the cut glass fibers can be varied by varying the diameter of the forming package during winding of the glass fibers or by rewinding the glass fibers from the forming package onto a smaller or larger diameter package. The many layers of glass fibers which are removed from the package can be laid flat on a supporting surface. The supporting surface can be a plate or tray or moving conveyor belt. Generally, the discrete lengths of glass fibers obtained by this approach can range from about 1 inch to around 25 inches. Any other method for removing the glass fibers from the multilayered package can be employed. For example, the fibers can be unwound from the package and disposed as chopped strand or continuous strand onto another supporting surface or holder or rotating drum. Preferably, the discrete lengths of glass fibers can range from about 0.25 inch (0.64 cm) to around 70 inches (180 cm) and most preferably only up to around 25 inches (64 cm).

Before the pores are generated in the glass fibers as fibers or strands, any sizing composition present can be removed through a solvent wash to remove the solvent soluble sizing composition, for example, a water wash can remove most of the water soluble sizing composition. It is preferred not to remove the sizing composition from the glass fibers, since the sizing composition appears to play a protecting role in any heat treating and acid leaching steps used in generating pores.

The pores can be generated in the glass fibers by several routes, depending upon the filament diameter of the glass fibers and/or the composition of the glass fibers. The pores that are generated should have a diameter across some portion of the opening of the pore, whether the pore is circular, eliptical, cylindrical or asymmetrical in shape, comparable to the MED of at least the related material, or the biochemically active material and, if used, the one or more chemical attaching agents. The mean pore diameter of the pores generated can have a broad or narrow distribution as long as the majority of pores have a pore diameter that is greater than the MED of the related material, or biochemically active material and, if used, the one or more attaching agents to allow these material to enter the majority of pores.

For glass fibers that are heat treatable for phase separation, the fibers are heat treated in a furnace or on a heated drum on which they were wound. The heat treatment is usually at a temperature greater than the annealing temperature and less than the softening point temperature of the glass. The fibers can be water leached before they are acid leached, where the heat treatment, water leaching and acid leaching are conducted in accordance with the teachings of U.S. Pat. No. 3,843,341 hereby incorporated by reference. Some glass fibers with higher amounts of boron-containing material can have pores of sufficient dimensions generated by heat treatment for phase separation followed by water leaching alone. Other glass fibers having around 20 to less than 30 or 35 weight percent boron oxide or anhydride can have heat treatment for phase separation followed by water and/or acid leaching or merely acid leaching as described in U.S. Pat. Nos. 4,042,359; 2,106,744 and 3,485,687, all hereby incorporated by reference. When the glass fibers have a composition of alkali metal oxides and siliceous material without any boron-containing material, the glass fibers can have pores generated without heat treatment or water leaching. This type of glass fiber is typically acid leached.

When solid glass fibers of a borosilicate composition have a fiber diameter of less than around 15 to about 20 microns, pores can be generated in the fibers by acid leaching without heat treatment in the manner shown for fibers with diameters of less than 0.001 inch (25.4 microns) in U.S. Pat. No. 2,461,841, hereby incorporated by reference. Also for hollow glass fibers having a glass composition of the alkali metal borosilicate ternary system and a wall thickness of around 15 microns or less, pores can be generated through acid leaching without heat treatment. Hence, glass fibers of "E-glass" and "621 glass" in solid or hollow fibers can be made porous through acid leaching without the necessity of heat treating before acid leaching.

Porous glass fibers having pores generated from glass composition with large amounts of water and/or acid leachables have a substantial amount of these leachable materials removed during leaching which usually results in satisfactory pores. Porous fibers having pores generated from just acid leaching ordinarily have mean pore diameters and pore volumes below those that are required. Nonexclusive examples include when the glass fibers have a composition with an effective amount of water and/or acid leachable components to result in at least a minor degree of interconnecting of water and or acid leachable components, or when the fibers have a diameter or wall thickness of less than around 20 and 15 microns, respectively. In these cases, the desired mean pore diameter and pore volume are achieved by not only heat treatment and water and/or acid leaching but also by alkali leaching. Alkali leaching increases the size of generated pores through the removal of any residual boron-containing material, alkali metal and/or earth metal oxides and some siliceous material. Since alkali treatment removes some of the silica, alkali treatment must be carefully controlled to insure against excessive removal, when discrete fiberous lengths are desired.

An alkali leach to remove colloidal silica from the pores and some silica of the silica-rich fibers to yield porous fibers of discrete lengths involves contacting the fibers with an alkali solution generally equivalent to about 0.5 normal sodium hydroxide at 25° C. for about 2 hours or less. The alkali solution may be more or less concentrated with a commensurate adjustment in the time of alkali treatment. Nonexclusive examples of bases equivalent to sodium hydroxide that can be used in alkali leaching include other alkali metal or alkaline earth metal hydroxides, mono-di- or triacid bases, and other inorganic and organic basic material equivalent to these in leaching ability. The alkali leach can enlarge the pores to the desired mean pore diameter and to the desired pore volume to correspond to the desired MED. Between any of the leaching steps it is preferred to wash the fibers with water.

To produce fiberous particles which still maintain characteristics of fiberous curvature, the pore volume of discrete lengths of fibers in increased beyond that desired for the discrete lengths of fibers. This can be accomplished through vigorous alkali leaching by using more concentrated alkali or longer treatment times or higher treatment temperatures. Also, the increase can be obtained by having a low amount of non-water and non-acid leachables in the glass fiber composition, and remove the high amount of water and/or acid leachable components from the glass fibers.

The porous glass fibers of the invention, whether solid or hollow, are silica-rich, around 90% or more silica, and have a mean pore diameter controlled to be in the range of about 10 to about 3,000 angstroms from any of the aforementioned pore generating operations. The lengths vary from the particulate to continuous fibers, where discrete lengths of fibers have a pore volume in the range of about 0.5 to about 1.5 preferably about 0.5 to about 1.2 and fiber diameters from about 3 microns to 150 microns or more. To these glass fibers, the biochemically active material is applied and becomes associated with the glass fibers either by adsorption directly onto the glass surface or by entrapment through precipitation or by covalent bonding through a linking agent, or by crosslinking with a crosslinking agent.

In applying the biochemically active material to the porous glass fiber, where the biochemically active material is adsorbed on and into the glass fiber, the application is by combining the two materials. This combination can occur, for instance, in a column process in which the glass fibers are packed in a column, or in a batch process in which the glass fibers are dispersed in a vessel or are submerged and surrounded by the biochemically active material in a vessel. In immobilizing the biochemically active material on the glas fibers, a medium can be used to maintain the activity of the biochemically active material. Any medium may be employed which does not deactivate the particular biochemically active material. Preferably, pH buffered aqueous solutions are used for the nonliving biochemically active material. The solutions are adjusted to the various pH requirements of the particular biochemically active material in orde to maintain the activity of the species without denaturing it. For example, useful pH buffered aqueous solutions include: acetate buffers of pH 4 to 6, phosphate buffers of pH 6 to 8, borate buffers to pH 8 to 9, and these can be used for enzymes, proteins and nonliving cells or parts of cells with activity levels in these pH ranges. For living cells and parts of cells and some immunological materials, the medium also includes nutrients to maintain the living activity of these biochemically active material. Any nutrient medium or culturing medium known to those skilled in the art of biochemistry and/or cellulor biology to be useful for specific cells or parts of cells can be used.

The adsorption is performed at a temperature at which the biochemically active material is not deactivated, usually at about 0° C. to about 40° C. The amount of biochemically active material used may be as much as that which saturates the adsorption capacity of the porous glass fibers. The quantity adsorbed on the glass fibers can be determined by the presence or absence of a degree of activity of the biochemically active species in an inert medium or by subjecting the immobilized biochemically active material to biochemical activity assay as known to those skilled in the art or by any other method known to those skilled in the art. For instance, a total protein assay can be conducted or a percentage of activity of total protein can be determined.

In bonding the biochemically active material to the porous glass fibers by the covalent bonding method, any known dual functional linking agent which has an inorganic functional moiety and an organic functional moiety can be used. The inorganic moiety attaches to the internal and external surfaces of the porous glass fibers and has the organic moiety available for covalent bonding with any reactable organic moiety of the biochemically active material. Examples of these linking agents include organofunctional silane coupling agents, organofunctional titanate complexes and any other organofunctional coupling agents known to those skilled in the art to be used with glass fibers. Also the linking agent can be a combination coupling agent, where the organo functional coupling agent is reacted with an intermediate compound which is reactable with the biochemically active material. An example of this method includes reacting a material such as glutaraldehyde with an amino-organo functional silane and either applying the reacted organo functional silane to the porous glass fibers or applying the amino-organo functional silane to the porous glass fiber and then treating the silynated glass fiber with the glutaraldehyde. A particularly suitable linking agent which can be used without an intermediate compound is the silyl aldehyde coupling agent available from Union Carbide under the trade designation Y9657. This material is unhydrolyzed, partially hydrolyzed, or fully hydrolyzed form is applied to the glass fibers. The silyl portion of the molecule reacts with the glass fiber surface leaving the aldehyde portion of the molecule available for reaction with the biochemically active material.

The organo functional coupling agent is applied to the porous glass fibers preferably in an aqueous treatment by having the porous glass fibers submerged in, sprayed with or contacted by the aqueous solution having the organo functional coupling agent. When an intermediate compound is used, it can also be applied in the same fashion and maintained in contact with the glass fiber for a period of time and at such temperatures to optimize the reaction of the intermediate compound with the linking agent. Examples of the intermediate compounds include the following: hexamethylene diisothiocyanate, toluene diisocyanate, xylene diisocyanate, glutaraldehyde, dialdehyde starch, dimethyl adipimidate, dimethyl suberimidate, dimethyl-3,3'-dithiobispropionimidate, succinic acid anhydride, croton aldehyde, acrolein, and the like material alone or in combination, whereby said compound is bonded to the biochemically active material directly or through an intermediate spacer compound such as lysine, hexamethylene diamine, and the like.

Also, the glass fibers and the biochemically active material can be attached by using water-soluble crosslinking agents that crosslink with the biologically active species, such as 1-ethyl-3-(3-dimethyl-aminopropyl)carbodiimide to hold the biologically active species in the pore of the fiber. The linking or crosslinking reactions as set forth above are carried out in an inert medium, for example, an aqueous medium which may contain tetrahydrofuran, acetone, ethanol, and the like. Said reaction may be conducted preferably at room temperature and at a pH at which the biochemically active material can be stable, generally in the range from 4 to 12. The linking agent may be used in an amount of around once to twice as much as the moles of the free groups to be bonded. Any known linking and/or crosslinking agents for use with biochemically active material and supports can be used in chemically attaching the biochemically active material to the porous glass fibers.

It is also preferred before applying the linking agent or the linking agent and intermediate compound or the biochemically active material for adsorption that the porous glass fibers be air dried to generate additional hydroxyl groups. Also, the porous glass fibers having the linking agent and/or linking agent and intermediate compound for covalent bonding with the biochemically active material preferably can be and preferably are dried under vacuum to remove any entrapped air before application of the biochemically active material. The biochemically active material is then applied to the glass fibers in a similar manner as when the species is applied to the glass fibers for the adsorption bonding. When the biochemically active material constitutes cells, living parts of cells, or immunological materials, the biochemically active material can be in a nutrient or culture medium when contacted with the porous glass fibers having the linking agent or the like.

When the biochemically active material constitutes cells, living parts of cells, or immunological materials, the biochemically active material can be in a nutrient or culture medium when contacted with the porous glass fibers having the linking agent or the like. The medium composition, medium pH, medium flow rate, container dimensions, culture conditions, such as temperature, gaseous activating fluid composition and the like factors all are dependent, to some degree, on the particular type of cellular biomaterial employed and the desired process parameters and goals. Such factors can be determined readily by those skilled in the art. For example, known cell lines have been immobilized and cultured on polymer supports with the use of specific culture medium and conditions. These established mediums can also be used with the present invention. Also any method known in the art for conducting small scale compatibility testing of various culture mediums with specific types of cells can be used.

One suitable method for linking the cellular biomaterial to the glass fibers involves the use of amine organosilanes and collagen and lysine. The glass fibers are treated or sized with a dimethylaminosilane like dimethylaminoethyltrimethoxysilane or dimethylaminopropyltrimethoxy silane or their hydrolysis products or with any other organo coupling agent. The collagen through the epsilon amino group of lysine is attached to the silynated glass fiber by known chemical techniques. The material is now available for immobilization of the cellular biomaterial to the glass surface.

With the biochemically active material immobilized on and/or in the porous glass fibers, an environment can be maintained for the fibers to retain most of, if not all of, the biochemical activity. The environment is provided by surrounding the fibers with stabilizing fluids like nutrient or culture fluids for living biochemically active material or with pH buffered aqueous solutions, or with particular temperature conditions. A particular suitable maintenance environment is provided by freeze drying the fibers using ice or some other known inert coolant. Of course, the biochemical or biological activity of the immobilized biochemically active material can be less than 100 percent of the immobilized material. At least a substantial minority and preferably a majority of the immobilized material should be active when immobilized and during and after maintaining the activity.

In preparing the porous glass fibers with immobilized biochemically active material, it is preferred to maintain an alignment of the fibers of fairly uniform parallism to each other during pore generation and immobilization. The maintenance of this alignment assists in producing packed columns of the glass fibers with immobilized biochemically active material. As a nonexclusinve example, this alignment can be accomplished by placing a restraining device perpendicular to the lengthwise axis of the glass fiber after the fibers are cooled following heat treatment. The glass fibers can then be placed in a tubular or column rector for subsequent leaching and immobilization. Any other method or device of aligning the fibers known to those skilled in the art may be used. In addition to the porous glass fibers that were aligned for facile introduction to vessels with immobilized biochemically active material, the glass fibers can be prepared into mats, paper, cloth and other forms which may be treated as above described for subsequent use in the immobilization of biochemically active materials.

The immobilized biochemically active material prepared in accordance with the present invention has a noticably good activity of biochemically active material. The immobilized material in the glass fibers is useful for various purposes depending on the specific characteristics of the immobilized biochemically active material. Accordingly, by providing a system of the immobilized biochemically active material and a system containing a substance sensitive to the activity of the biochemically active material, for example, a substrate in the case where the biochemically active material is an enzyme, which may be present with a buffered solution, a product of the enzymatic reaction can be collected and quantitative analysis of the substrate can be made.

Substrates that can be utilized with the present invention, include aqueous solutions, aqueous medium, for example, buffered solutions, and those of bodily fluids such as siliva, urine, serum or treated liquids thereof. For example, when an acylase is to be employed as the enzyme, the substrate may be a solution of a 7-acylcephalosporanic acid derivative, a solution of 6-acylpenicillanic acid derivatives or a solution of 7-amino-3-cephem-4-carboxylic acid or its derivatives, or 6-aminopenam-3-carboxylic acid or its derivatives and methyl thienyl acetate or methyl-aminophenyl acetate. When colineoxidase, various phospholipase, uricase or glucoseoxidase is to be employed, a substrate may be used corresponding to phospholipids, uric acid, glucose, and body fluids such as blood, serum or urine. Generally, the substrate is used to protect a biochemically active site on the biochemically active material either before, during or after immobilization on the porous glass fibers.

The macroconfiguration of the porous glass fibers results in improved microconfiguration of the mean pore size and pore volume. The porous glass fibers yield good internal surface volume which can allow for the linking and/or crosslinking agent and the biochemically active material with their MEDs to enter the pores and become attached to the glass surface directly or indirectly. Also, the mean pore diameter is large enough to provide low diffusional resistance to substrates and chemical or biochemical products or the biochemically active material. The porous glass fibers with immobilized biochemically active material have the high ratio of surface area to pore volume with immobilized biochemically active material to provide good diffusional characteristics.

In addition, the porous hollow glass fibers with immobilized biochemically active species have good enough diffusional characteristics and the proper MED for the biochemically active related material such as raw material or nutrients to flow either in the lumen or around the exterior surrounding area of fibers. The immobilized biochemically active material can utilize such a supply stream that may pass through the pores and the immobilized biochemically active material can relinquish a product or waste stream. This stream can flow through the pores and be collected from the exterior surrounding area or lumen, respectively. For example, porous hollow fibers with immobilized biochemically active material like living cells or parts of cells can be utilized for growing these biochemically active materials for harvest. In a perfusion tissue culture technique, the biochemically active material on the walls of the fibers could receive nutrients supplied through the pores or release metabolic wastes through the pores for collection. The biochemically active material would be periodically harvested from the fibers.

FIG. 1 depects the glass fibers 10 with immobilized biochemically active material vertically disposed in container 12. The container 12 also has environment 14 to maintain the biochemical activity in the interstices between and surrounding the vertically arranged fibers. The container has an inlet port 16 and an outlet part 18. Also the container can have a sufficient structure to allow for elevated or reduced temperatures and/or pressures within chemical engineering parameters. The porous glass fibers with immobilized biochemically active material are packed in the container 12 with sufficient room between them to allow the environment 14 to contact the surfaces of the glass fibers. Generally, the separation between fibers is in the order of magnitude of at least microns.

PREFERRED EMBODIMENT FOR THE INVENTION

The glass forming fiberizable pore generating batch composition is formulated by back calculations to result in glass fiber compositions that are heat treatable for phase separation into the water and/or acid leachable components and the non-water and non-acid leachable components like alkali metal borosilicate glass compositions. The formulation also allows removal of a substantial portion of the former components through water and acid leaching without the necessity of alkali leaching to achieve discrete lengths of glass fibers with sufficient pore diameters and volume.

The glass fiber forming batch most preferably provides fibers with a glass composition having about 54 weight percent $B_2O_3$, 8 weight percent $Na_2O$, and about 38 weight percent $SiO_2$. This glass composition is formed by melting the batch at about 2282° F. (1250° C.) for 2 hours and is formed into glass fibers at about 1610° F. (877° C.) by mechanical attenuation from a bushing. The fibers formed have a diameter in the range of about 3 microns to about 150 microns and most preferably for handling purposes, about 3 microns to about 40 microns. Most preferably, the fibers are formed into hollow glass fibers with an outer diameter in the aforementioned range and an internal diameter to give a K factor in the range of up to about 0.9. The K factor is the ratio of inner diameter to outer diameter. The air flow to the hollow fiber bushing is satisfactory to result in the desired K factor and for a ten tip bushing is usually in the range of greater than 0 to about 0.5 cfm (cubic feet per minute). The glass fibers are sized with an aqueous chemical treating composition preferably having a film forming polymer like epoxy resin, which is water soluble, dispersible or emulsifiable, and water soluble lubricant like Cation-X ® lubricant and a compatible organosilane coupling agent like an epoxy silane. The appropriate amount of size is applied to protect the fibers from interfilament abrasion, but not too high an amount to have a large amount of moisture present, which might be detrimental to the high boron-containing fibers. The fibers are gathered into one or more strands and wound into a cylindrical forming package.

A plurality of undried forming packages are cut along their longitudinal axes so that all of the layers of glass fibers can be removed from the package. These fibers are laid straight on trays in a nearly parallel alignment, where the fibers usually have a discrete length of about 25 inches (63.5 cm).

The fibers are heat treated at a temperature in the range of about 420° C. to about 600° C. for a period of time from about 10 minutes to several days. Longer times require lower temperatures while shorter times require higher temperatures in these ranges. Most preferably, the fibers are heat treated at 540° C. for 6 hours to phase separate the glass fibers into an insoluble phase and a soluble phase which is the water and/or acid leachable material. For the glass fibers with higher amounts of boron-containing materials, lower heat treating temperatures are useful to decrease any sticking together of the glass fibers, while the presence of a protective size allows utilization of higher heat treating temperatures. Afterwards, the fibers are cooled to ambient temperatures.

The glass fibers are leached, with water followed by an acid leach. In the water leach, the glass fibers are immersed in a water bath for a sufficient period of time, at a sufficient temperature to remove a substantial amount, if not all, of the water soluble boron-containing compounds in the glass fibers. The glass fibers are submerged in the water when the water is cool and the temperature of the water is increased to an elevated temperature preferably around 80° to 100° C., most preferably around 95° C., for 1 to about 24 hours, preferably 3 hours. It is preferred that the water leaching step be performed in a vessel that accommodates agitation which is performed during the water leaching step. If the temperature of the water bath falls below 80° C., there is less thorough leaching and there must be a substantial increase in the leaching times. The time of leaching depends on the temperature of the bath and the size of the fiber being treated. In order to keep the fibers aligned during the leaching process, they are immobilized usually by placing a rod perpendicular to the long axis of the fibers to hold them stationary. The volume ratio of water to glass fibers in the leaching bath can be about 2 to 8 volumes of water to one volume of glass fibers. Low water to glass fiber volume ratios slows the leaching process while a higher volume ratios serve no particular advantage.

After water leaching, the glass fibers are removed from the water solution. The glass fibers are than acid leached, with agitation, in a dilute acid solution, such as 0.1 to about 3 Normal, preferably, about 0.1 to 0.5 Normal hydrochloric acid, at temperatures around 80° C. to 100° C., preferably 90° C., for about 10 minutes to about 8 hours, preferably about 2 to about 4 hours. Generally, the dilute acid solution removes any remaining traces of boron, alkali metal oxides and alkali metal borates so that the pores are unplugged of these material. Nonexclusive examples of other suitable dilute solutions of acids include sulphuric and nitric acid, or organic acids such as oxalic acid. The volume ratio of acid to glass fibers in the acid leaching step can be about 1 to about 8 volumes of acid to one volume of glass fibers which will vary somewhat with the normality of the acid. The glass fibers are removed from the acid leaching solution, water washed to a pH of around 5.5 to neutral in the wash water after which the fibers are dried, preferably in air drying at around 90° C. for around 10 minutes to about 24 hours.

The porous glass fibers are subjected to air oxidation to remove any carbonaceous residue in the pores that may result from the sizing composition being present on the glass fibers during heat treatment. The temperature of oxidation is that sufficient to oxidize carbon in the presence of an adequate amount of oxygen preferably provided by flowing dry reconstituted air. It is most preferred that the oxidation is conducted at around 1000° F. (537° C.) or higher for about 20 minutes up to about 2 hours. The oxidation temperature should not be of such magnitude that the glass revitrifies and closes most of the pores or significantly reduces the strength of the porous fibers.

The porous glass fibers than undergo silanization with a solution of an organosilane coupling agent, most preferably, gamma aminopropyltriethoxy silane, at an elevated temperature most preferably around 75° C. for about 2 to about 3 hours. The concentration of the amino silane in the aqueous solution is most preferably around 10 weight percent and has a pH of around 3.75. The silynated fibers are removed from the organo silane coupling agent solution and most preferably, they are treated with a crosslinking agent which is most preferably about 10 weight percent glutaraldehyde in a 0.5 mole phosphate buffer solution having a pH of 7 at ambient temperature for around 2 hours in a vacuum oven. The vacuum is applied to remove any air entrapped in the pore structures. After crosslinking, the porous glass fibers are thoroughly washed with distilled water. This water washing assists in assuring a presence of a desired minimum, efficient amount of silane. This amount most preferably results in a near monolayer of the silane on and in a substantial portion of the porous glass fibers. Although amounts resulting in coverage of less than a monolayer of silanes can be used, these amounts will not give the maximum loadings of the biochemically active material. Larger amounts should be avoided since they may unnecessarily reduce the pore diameters.

The biochemically active material which is preferably an enzyme for immobilization in the pores of the porous glass fibers is prepared in a solution of adequate concentration, with appropriate buffers and appropriate pH which may vary somewhat for different biochemically active material. As an example, a solution of one percent enzyme can be 100 milliliters containing 1 gram of amyloglucosidase and 3 grams maltose in a 0.5 molar acetate buffer having a pH of 4.7. The solution is contacted with the glass fibers preferably maintained in parallel alignment usually at any nondenaturing conditions to soak the fibers with the solution. The contacting can be performed at a less than ambient temperature, most preferably at around 4° C. for about 1 hour with occasional agitation. The glass fibers with immobilized enzyme were water washed a number of times with distilled water to insure the complete removal of free enzyme. The presence of the maltose is as a stabilizing agent to stabilize the activity of the amyloglucosidase by a complex formation during the immobilization.

The preferred embodiment and other alternative embodiments are further illustrated in the following examples.

EXAMPLES

TABLE 1

| SAMPLES | $B_2O_3$ | $Na_2O$ | WEIGHT % $SiO_2$ | $ZrO_2$ | $Al_2O_3$ | CaO |
|---|---|---|---|---|---|---|
| 1 | 7.2 | 1.0 | 54.0 | — | 14.3 | 22.4 |
| 2 | 7.2 | 1 | 54.0 | 3.6 | 10.7 | 22.4 |
| 3 | 27.0 | 8.0 | 60.0 | 3.6 | 1.3 | — |
| 4 | 23.0 | 8.0 | 69.0 | — | — | — |
| 5 | 54.0 | 8.0 | 38.0 | — | — | — |
| 6 | 41.0 | 8.0 | 51.0 | — | — | — |
| 7 | 54.0 | 8.0 | 35.0 | 3 | — | — |
| 8 | 0 | 29 | 62 | 9 | — | — |

The glass compositions listed in Table 1, which may also have trace amounts of impurities, can be useful in immobilizing various biochemically active material. The process for immobilizing the biochemically active material varied depending upon the glass composition and the method, either chemical or adsorption, for immobilization. The glass fibers that are formed with the glass compositions of Sample 1 through Sample 4 of Table 1 should be alkali leached to some degree in addition to acid leaching and possibly water leaching for use with biochemically active material having larger minimum exclusion diameters. Samples 1, 2, 3, 4 and 8 of Table 1 do not require heat treatment for resultant phase separation and pore generation. The glass fibers formed with the compositions of Sample 3 through 7 can be heat treated for phase separation and are water and acid leached. Samples 5 through 7 do not require alkali leaching for achieving the desired MED. The glass fibers having the glass composition of Sample 8 acid leached with a stronger concentration of acid and undergoes alkali leaching for larger MED biochemically active material. Generally, either chemical bonding or adsorption techniques for immobilization can be used with any of the glass fibers of Table 1.

EXAMPLE I

IMMOBILIZATION OF GLUCOAMYLASE ON GLASS FIBERS OF SAMPLE 5

The material included: amyloglucosidase available from Sigma Chemical Company under trade designation No. A7255; gamma-aminopropyl triethoxy silane (A1100) available from Union Carbide Corporation; maltose available from Sigma Chemical, Grade 1, designation M-5885; glutaraladehyde in a 25% solution used as a linking agent is available from Fisher Scientific Company.

Details:

A batch composition calculated to yield the desired oxide amounts in the glass composition of Sample 5 of Table 1 was melted in platinum crucibles at 2282° F. (1250° C.) for 1 hour with occasional stirring. A 10 nozzle glass fiber bushing was charged with glass and conditioned at 2000° F. (1093° C.) for 1 hour to remove seeds from the melt. The tip plate was then set for a 1600° F. (871° C.) temperature and the melt thermocouple reads 1687° F. (919° C.). Glass fibers were formed by mechanical attenuation onto an 8 inch collet that was rotated at 295 RPM to form 70 micron solid fibers. During their formation, the fibers were treated with an aqueous solution having 0.5 weight percent Cation-X ® lubricant and 0.5 weight percent gamma-glycidoxypropyltrimethoxy silane. The fibers were sliced off of the package resulting in multiple layers of 25" long fibers×70 micron OD.

The fibers were laid on a flat surface were heat treated for 6 hours at 540° C. in a Blue-M muffle furnace. The phase separated fibers were cooled slowly to prevent thermal shock over a 1 hour period to ambient temperature. After cooling, the fibers were placed in 6 volumes of water (4.0 micron mhos/cm) in multilayered near parallel alignment and maintained in this position by a retaining bar. The water was heated to 95° C. in ½ hour and held with gentle agitation for 6 hours.

After leaching a substantial amount of the boron and sodium oxides from the fiber, the water should be drained, and 0.3N HCl was introduced into the bath and heated to 95° C. The fibers were soaked in this bath for 4 hours with agitation. The HCl was drained and the fibers were washed with distilled water until a pH of around 5.5 to neutral was achieved. The fibers were then dried in flowing air at 95° C. for 4 hours. Traces of residual carbon were removed from the leached fiber by a 2 hour oxidation treatment in air at 1000° F. (538° C.). The fibers were then placed in a 10% A1100 solution at 75° C. for 2.75 hours. The fibers were water washed to remove residual A1100 and dried overnight at 95° C. The amino silynated fibers were contacted with a 2.5% glutaraldehyde/phosphate buffered solution having a pH of around 7 under vacuum at room temperature for 2 hours. The fiber turned a deep magenta color due to the reaction of the aldehyde with the amino group of the silane. The fibers were then water washed to remove excess glutaraldehyde.

A solution of 1% glucoamylase/3% maltose in 0.5M acetate buffer (pH 4.7) was contacted with the activated porous fiber at 4° C. for 1 hour. The fibers were water washed to remove unbound enzyme, and they were placed in a 1% starch solution at 45° C. with agitation. Samples were taken at 3 minute intervals and the glucose concentration was measured by injecting each sample in a YSI27 glucose analyzer available from Yellow Springs Instrument Corporation. The enzyme activity was compared with the activity of a known amount of free glucoamylase through placement of three milligrams of the glucoamylase into the 1% starch solution at 45° C. The active enzyme concentration per gram of glass fiber was determined.

EXAMPLE II

IMMOBILIZATION OF GLUCOAMYLASE ON HOLLOW POROUS GLASS FIBERS OF SAMPLE 3

The material included:
0.5N NaOH
3N HCl
Distilled water (4 mhos/cm conductivity)
Glucoamylase available from Sigma Chemical under the trade designation No. A7255)
aminopropyl triethoxy silane (A1100) material from Union Carbide Corporation, and
Glutaraldehyde The Sample 3 glass composition of Table 1 was produced by melting glass forming batch calculated to yield the desired quantities of oxides melted at a temperature of 2600° F. (1427° C.) for 3 hours in platinum crucibles. The melt was cooled and crushed into approximately 0.5 inch (1.27 cm) pieces and charged into a 4 tip hollow fiber bushing. The fibers were drawn on an 8" collet (20.32 cm) rotating at 135 RPM after a 1 hour conditioning in the bushing melter at 2600° F. (1427° C.) to reduce the seed content of the glass. Air flow to the tips was set at 0.5 ft$^3$/min (cfm). The fiber physical dimensions were:
Outer diameter (OD)=77 m
Inner diameter
(ID)=38.5 m
K=0.5 (K=ID/OD).

The fibers were cut from the package in 25" lengths. Without heat treatment, the fibers were leached in 3N HCl for 1 hour at 95° C.

The fibers were water washed with distilled water until a pH of 5.6 was achieved. The total weight loss was 36% with a glass fiber composition of 95% $SiO_2$, 5% $ZrO_2$. The pore size averaged 8-20A with a surface area of 400+m$^2$/gm.

Two specimens of these porous fibers were prepared for enzyme immobilization. The first specimen was prepared as aforedescribed with no alkali leaching. The second specimen was prepared as aforedescribed but in addition the glass fibers were alkali leached. Both specimens were coated with A1100 gamma-aminopropyltriethoxy silane at 70° C. for 2.75 hours. After water washing to remove excess A1100, the fibers were dried overnight at 95° C. under vacuum.

The fibers were covered with a 1% glucoamylase/3% maltose solution in pH 4.7 acetate buffer for 1 hour at 3° C. The fibers were water washed 6 times with distilled water to remove unbound enzyme. The fibers were placed in a 1% starch solution at 45° C. and agitated. The glucose production was measured and the amount of bound active protein determined by comparison with free enzyme activities as in Example I and gave the following results:

| Specimen | mg/gm Active Enzyme |
|---|---|
| 1 | 0.88 |
| 2 | 2.08 |

The results show an increase in the loading of active enzymes for the alkali leached specimen which leads to the conclusion that the pore size was increased by alkali leaching.

EXAMPLE III

GLUCOAMYLASE IMMOBILIZED ON POROUS GLASS FIBER OF SAMPLE 5 USING ADSORPTION TECHNIQUES

The glass fibers were prepared as outlined in Example I. Since adsorption was the method of enzyme attachment in this experiment, the A1100 coating and glutaraldehyde coating steps were eliminated. Instead, the glass fiber was fired at 537° C. (1000° F.) for 2 hours then cooled and stored in a closed container until time of analysis. An enzyme solution (50 ml/g as prepared in Example I) was placed in contact with the porous fiber at 4° C. for 1 hour. The fibers were removed from the solution, washed 6 times with distilled water and the last time with an acetate buffer of pH 4.7 to remove unbound enzyme. The enzyme activity was measured against the activity of 3 mg of free glucoamylase at 45° C. The result of this method yielded an enzyme loading of 25 mg of active enzyme/gram of glass fiber.

EXAMPLE IV

LACTASE IMMOBILIZED ON POROUS GLASS FIBER OF SAMPLE 5

Materials:
Beta-galactosidase (Sigma Chemical)
Details:
Porous glass fibers were prepared as in Example I with the exception that the heat treatment was conducted at a temperature of 560° C. for 4 hours instead of 540° C. due to the larger pore requirements for the larger enzyme galactosidase. This established that increasing the temperature of the heat treatment increases the pore size to accommodate larger MED biochemically active material. Two fiberous samples were prepared:

The first specimen was treated with A1000 plus glutaraldehyde for covalent coupling of the enzyme to the glass fibers.

The second specimen was uncoated porous glass fibers for adsorption of galactosidase.

Specimen 1 was washed several times in distilled water to remove excess glutaraldehyde. The fibers were then placed in contact with an 0.5% lactose/1.5% B-galactose solution in pH 7.0 buffer. The contact time was 2.0 hours at 3° C.

The unbound enzyme was washed away with distilled water. The fiber was then placed in a stirring lactose solution and the sugar conversion rate was measured with time using an automatic YSI27 glucose analyzer, which indicated enzyme activity for both specimens.

EXAMPLE V

GLUCOAMYLASE IMMOBILIZED ON GLASS FIBERS OF SAMPLE 5 USING AN ALDEHYDIC SILANE AS LINKING AGENT

Additional Materials:
Silyl aldehyde (Y9657) from Union Carbide
Details:
Silylaldehyde was reverse hydrolyzed for coupling to the glass surface by the following method:
a. 1 part Y9657 was mixed with 3 parts ethanol and stirred for 20 minutes (methanol can be used if more available).
b. To this solution, ½ part acetic acid was added with stirring.
c. Finally, ½ part water was added to the mixture and stirred for an additional 20 minutes.
d. This solution was added slowly to distilled water with stirring to prepare a 2% Y9657 solution.

Glass fibers prepared as in Example I were covered with the silyl-aldehyde solution at room temperature and soaked for 4 hours. The silane was drained and the fibers then water washed and subsequently dried at 95° C. overnight.

The silynated fibers were contacted with a solution of glucoamylase and maltose as described in Example I. The fibers were water washed to remove unbound enzyme. The bound enzyme was assayed by measuring the production of glucose in a 1% starch solution as in Example I. The final enzyme loading was 9.2 mg of active enzyme/gram of glass fiber.

EXAMPLE VI

GLUCOAMYLASE IMMOBILIZED ON POROUS GLASS FIBER OF SAMPLE 5 USING SILYL ALDEHYDE AND GLUTARALDEHYDE AS LINKING AGENTS

Porous glass fibers were prepared as in Example V. Before the enzyme solution was added to the silanated fiber, the fibers were placed in a 2.5% glutaraldehyde solution to attempt to crosslink the silane with the glutaraldehyde and to extend the linking arm between the fiber and enzyme. After a 2 hour soak, the fibers were water washed to remove excess glutaraldehyde.

The fibers were then soaked in the glucoamylase solution of Example I. The fibers were again water washed and the amount of bound enzyme assayed using measured glucose production rates in a 1% starch solution as in Example I. A 10% improvement over straight Y9657 coated fibers was realized with an enzyme loading of 10.0 mg of active enzyme/gram of glass fiber.

EXAMPLE VII

CELLS BOUND TO THE SURFACE OF POROUS HOLLOW GLASS FIBERS OF SAMPLE 3

Materials:
Bound dependent cell line:
ATCC CRL 1392 (ATCC CL101)
LLC-PK1 (PIG KIDNEY)
REFERENCES: In Vitro 12:670–677 1976
Medium: Minimum Essential Medium—10 (MEM-10)
Eagle's MEM supplemented with 10 percent fetal calf serum.
Details:
Porous glass fibers of Sample 3 of Table 1 prepared as in Example II were dried and placed in contact with the cell line mentioned above. With cell medium around the fibers and cells, the cells were left in contact with the fiber for three days. Cell growth on the fibers was measured with an optical microscope after the three day incubation. Cells were seen growing on the surface and in the lumen of the hollow fiber. The cell growth was a continuous monolayer across all fibers. No cell bridging was noticed after the three day period.

EXAMPLE VIII

MONOCLONAL ANTIBODIES IMMOBILIZED ON POROUS GLASS FIBERS OF SAMPLE 5 OF TABLE 1

Monoclonal Antibody: Antibody to serum spreading factor (Inh-Mcl)
Ref.: Characterization of human serum spreading factor with monoclonal antibody Proc. Natl. Acad. Sc. USA Vol. 80 1362–1366 (1983).
Medium:
F12/DME (1:1) a 1:1 mixture of Ham's F-12 and Dulbecco's modified Eagle's (DME) media, supplemented with
Transferrin 25 mg/ml
Insulin 10 mg/ml
Ethanolamine 25 mg/ml
Selenium $5 \times 10^{-8}$M
Sodium Bicarbonate 1.2 g/l
10 milli Mole Hepes (pH 7.4) and antibiotics.
Ref.: Proc. Natl. Acad. Sci. 79, 1158–1162 (1982)

Details:

Specimens of A1100 silane coated and uncoated porous fibers of Sample 5 were prepared as described in Example I. The monoclonal antibody, produced from hybridoma cells line (Inh-Hyl), cultured in medium F12/DME (1:1) was purified by centrifugation. The A1100/glutaraldehyde fibers and uncoated fibers for adsorption were suspended in this antibody solution. Because of the low concentration of antibody, the entire amount (23 mg) was soaked into both fiber specimens. Both fiber specimens were checked for antibody pickup using the total protein determination by the Lowry technique. It is believed without limiting the invention that the antibody was covalently and physically bound on the surface of both fiber sets.

EXAMPLE X

DEOXYRIBONUCLEIC ACID (DNA) ADSORBED ON POROUS GLASS FIBERS OF SAMPLE 5 OF TABLE 1

Materials:

DNA: Purified Col E1 bacterial plasmid DNA

Radioactive label: 32P from New England Nuclear (contained in GTP) Plasmid labeled by nick translation Scintillation Solution: Scinti Verse Bio-HP (Fisher Scientific)

Buffer:
20 mM tris-HCl
2 mM EDTA
1M NaCl pH 7.4

Glass Fibers: Uncoated 500 A pore 80 m OD glass fibers of Sample 5 of Table 1 that were heat treated for 6 hours at 540° C. and leached according to Example IX.

Details:

Two inch long, 100 mg samples of the above mentioned glass fibers were placed in individual scintillation vials. Two microliters of radioactive labeled DNA (containing CA 220,000 cpm) was added to each fiber containing vial and also to an empty control vial. The solution was agitated for 30 minutes. At the end of 30 minutes, the solutions were decanted from each vial and centrifuged (2500 rpm for 5 minutes) for counting. Two milliliters of buffer were added to each vial and the vials were agitated for 5 minutes and decanted as above. An additional 2 milliliters were added to each vial, agitated, and decanted as above. A total of 10 milliliters of scintillor solution was added to each centrifuged washing contained in a scintillation vial. Additionally, 10 milliliters of scintillation solution was added to the washed fibers to be analyzed for 32P. Scintillation counting was conducted using a Beckman scintillation counter using external standardization. Results are listed in Table 2 and show that radiolabled plasmid DNA is adsorbed into the glass fibers. Deoxyribonucleic acid other than plasmid would behave in a similar fashion.

TABLE 2

| | TOTAL COUNTS (CPM) | | | |
|---|---|---|---|---|
| SAMPLE | WASH 1 | WASH 2 | VIAL + FIBER | Reaction Medium |
| 1 Control No fiber | 2,280 | 148 | 10,878 vial only | 220,804 |
| 2 100 mg fiber | 36,117 | 13,661 | 139,211 | 58,108 |
| 3 100 mg fibers | 39,873 | 15,999 | 105,128 | 90,539 |

EXAMPLE XI

COMPARISON OF ENZYME IMMOBILIZED ON POROUS GLASS FIBERS VERSUS POROUS GLASS BEADS

Porous solid glass fibers of glass Sample 5 having fiber diameters of 105 microns were prepared in accordance with the procedure of Example I with a few exceptions. These exceptions included that the fibers were not coated with an aqueous sizing composition and therefore, the air oxidation for removal of any residual carbon was not performed. The mean pore diameter of the porous glass fibers was determined to be around 500 angstroms.

Commercially available porous beads (CPG beads from Corning Glass Works) and the porous glass fibers as above-prepared were contacted with the amyloglucosidase solution of Example I in the same manner as Example I for both the beads and fibers.

Figure 2:
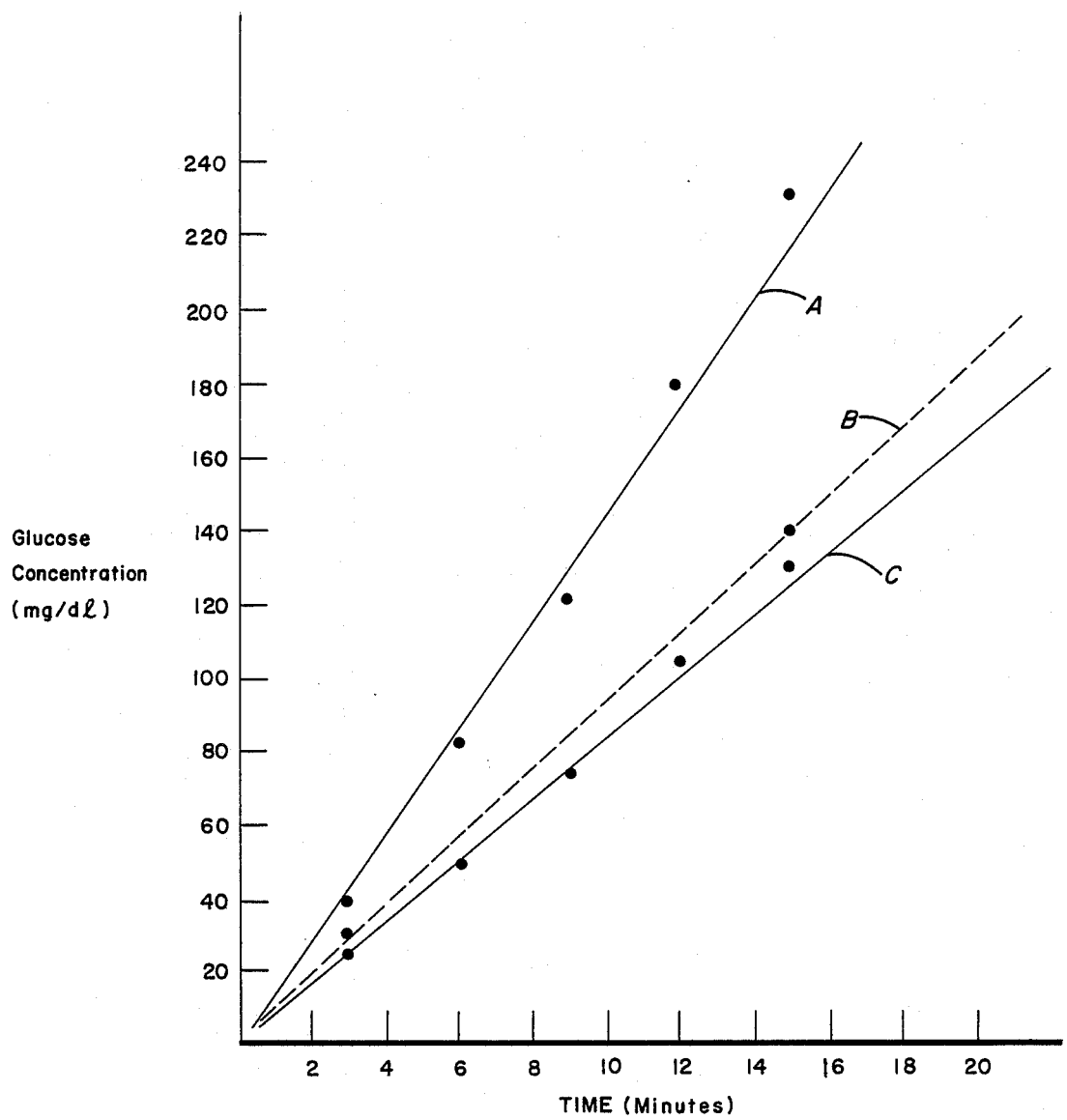
FIG. 2 is a graph of enzyme loading of glass fibers versus glass beads.

The enzyme activity was compared for the same weight of beads and fibers for conversion of starch to glucose as in Example I acid as further described infra. The sample times and glucose concentrations for the beads and fibers are given in Table 3 and the results are plotted in FIG. 2 along with those for the non-immobilized or free enzyme, line B. From the higher conversion, FIG. 2 shows a higher loading of enzyme on the glass fibers at line A of 4.8 mg enzyme/gm of fiber versus only 2.7 for the beads, line C.

TABLE 3

| Sample Time | Glucose Concentration in mg/dl for fibers | Glucose Concentration in mg/dl for beads |
|---|---|---|
| 3 | 33 | 26 |
| 3 | 32 | 25 |
| 6 | 74 | 50 |
| 6 | 72 | 50 |
| 9 | 119 | 77 |
| 9 | 118 | 76 |
| 12 | 173 | 104 |
| 12 | 173 | 104 |
| 15 | 218 | 129 |
| 15 | 218 | 132 |
| Slope | 15.7 | 8.8 |
| Free Enzyme Slope | 9.8 | 9.8 |
| Enzyme loading (mg enzyme/gm of fiber or glass) | 4.81 | 2.69 |

In the foregoing examples, the enzyme activity was determined by measuring the amount of reducing sugar produced from starch by the enzyme in the following manner.

A starch solution (1%) in 0.05M acetate buffer at pH 4.7 maintained at 45° C. in a 400 ml jacketed beaker with magnetic mixing was used as a substrate. After the immobilized enzyme was added to the starch solution, samples (1 ml) were taken at several time intervals. The enzyme reaction in the samples was stopped by the addition of ten microliters of 10% sodium hydroxide. The reducing sugar or dextrose concentration was then determined by the Somogy-Nelson method or by a Yellow Spring Instruments glucose analyzer.

The free enzyme activity was determined by using 3 mgs of enzyme in 100 ml of starch solution. The conversion to reducing sugar was measured in the same manner as for the immobilized enzyme.

The determination of the concentration of reducing sugar by the Somogy-Nelson method involved the following.

1. Reagents:

The alkali-copper reagent was prepared according to the procedure of Somogy-Nelson. Rochelle salt (12 g), sodium carbonate (24 g), sodium sulfate (144 gm), and sodium bicarbonate were dissolved in distilled water and diluted to 800 ml (Solution I). Sodium sulfate (36 g) and cupric sulfate (24 g) were dissolved in distilled water and diluted to 200 ml (Solution II). The reagent was readied for use by combining four volumes of Solution I with one volume of Solution II.

2. Analytical Procedure:

Samples were diluted with distilled water to a reducing sugar concentration range of 0.1 to 0.5 g/l. One ml of this sugar solution was mixed with one ml of alkali-copper reagent in a Folin-Wu sugar tube and heated in a boiling water bath for ten minutes. After cooling, one ml of arsenomolybdate was added and care was taken to dissolve all of the cuprous oxide. The resulting solution was then diluted to 25 ml with distilled water and read for absorbance at 580 nm with a Spectronic 20 photocolormeter. The amount of reducing sugar was determined by a standard curve which has been established by plotting the absorbance vs concentration of reducing sugar from a series of standard glucose solutions.

3. Data Analysis:

Control experiments were carried out to determine the stability of soluble starch at pH 4.7 and 45° C. in the presence of silane coated fiber glass or in the absence of fiber glass. Results indicated that no degradation of starch at these conditions occurred within five hours.

The determination of bound protein was conducted by the Lowry method in the following manner.

Reagents:

Stock solutions were prepared according to the following composition: Reagent A, 2% sodium carbonate in 0.10N sodium hydroxide; Reagent B, 0.5% cupric sulfate in 1% sodium or potassium tartrate; Reagent C, 1N Folin and Ciocalten phenol reagent. Reagent D was prepared fresh by combining 50 volumes of Reagent A with one volume of Reagent B.

Procedure:

Immobilized enzyme or protein standard was placed in a test tube and ten ml of Reagent D was added. The test tube was allowed to stand for ten minutes or longer at room temperature with occasional mixing. One ml of Reagent C was then added very rapidly and mixed with a second. After 30 minutes at room temperature, absorbance was read at 500 nm.

The foregoing has described a porous glass fibers with immobilized biochemically active material and the method of producing the glass fibers with the immobilized biochemically active material.

The glass fibers were immobilized biochemically active material of the present invention overcome any disadvantages of the inorganic surface to bond or absorb biochemically active material. Also, the fibers enable the utilization of the advantages of the excellent microbial resistance, excellent thermal stability to permit heat sterilization and reuse, and excellent dimensional stability to avoid distortion and destruction at elevated temperatures and pressures. Also, the fibers of the present invention are excellently suited for use in chemical, biochemical and biological reactors and reactions.

We claim:

1. Method of producing glass fibers with a discrete length having nonliving immobilized biochemically active material, comprising:
   a. forming sized glass fibers having a filament diameter from about 3 to about 150 microns and having a composition comprising greater than 35 up to about 60 weight percent $B_2O_3$, about 1 to about 10 weight percent alkali metal oxides, about 30 to about 65 weight percent $SiO_2$, up to about 5 weight percent $ZrO_2$, and up to about 4 weight percent $Al_2O_3$,
   b. gathering the sized fibers into one or more strands,
   c. collecting the one or more strands on a winder into a multilayered package,
   d. removing the one or more glass fiber strands from the multilayered cylindrical package,
   e. heat treating the glass fibers at a temperature in the range of about 400° to about 600° C. for a period of time of about 10 minutes to about 64 hours to phase separate glass into a boron-rich phase and a silica-rich phase,
   f. water leaching the glass fibers at an elevated temperature,
   g. acid leaching the glass fibers at elevated temperatures with dilute inorganic or organic acid solutions to produce porous silica-rich fibers having a pore volume of about 0.5 to 1.5 cc/gm,
   h. contacting the porous fibers with one or more nonliving biochemically active materials to immobilize the material in the internal surface area and on the external surface area of the glass fibers,
   i. maintaining the activity of the nonliving biochemically active material on and in the glass fibers.

2. Method of claim 1, which includes treating the glass fibers with an aqueous chemical treating composition before the fibers are gathered into strands, and a solid residue of the aqueous chemical treating composition is removed from the fibers before the fibers are contacted with the nonliving biochemically active material.

3. Method of claim 1, wherein the heat treated glass fibers are cooled at a rate of retard thermal cracking when leached.

4. Method of claim 1, wherein the porous glass fibers are dried to reduce the amount of moisture before being contacted with the nonliving biochemically active material.

5. Method of claim 1, wherein one or more chemical attaching agents are applied to the porous glass fibers before contacting with the nonliving biochemically active material, and the attaching agents are present in an effective amount for immobilizing the nonliving biochemically active material on the internal and external surfaces.

6. Method of claim 1, wherein the glass fibers are formed as hollow fibers having a K factor in the range of up to about 0.9, where the K factor is the ratio of internal to external diameter.

7. Method of claim 5, wherein the pores of the porous fibers have a minimum exclusion diameter such that the internal surface volume of the porous fibers allows for the linking agent and the nonliving biochemically active material to enter the pores.

8. Porous silica rich glass fibers containing immobilized nonliving biochemically active material prepared by the method of claim 1.

9. Porous silica rich glass fibers containing immobilized nonliving biochemically active material prepared by the method of claim 7.

* * * * *

UNITED STATES PATENT AND TRADEMARK OFFICE
CERTIFICATE OF CORRECTION

PATENT NO. : 4,748,121

DATED : May 31, 1988

INVENTOR(S) : R. P. Beaver et al

It is certified that error appears in the above-identified patent and that said Letters Patent is hereby corrected as shown below:

Title page:

In the References Cited - U.S. Patent Documents section U.S.

Patent No. 2,461,841   2/49   Nordberg   49/79   - should be inserted.

Signed and Sealed this

Twenty-seventh Day of December, 1988

Attest:

DONALD J. QUIGG

Attesting Officer

Commissioner of Patents and Trademarks